(12) United States Patent
Sullivan

(10) Patent No.: US 10,080,904 B2
(45) Date of Patent: Sep. 25, 2018

(54) DECIDING ON PATIENT ELECTRIC SHOCK THERAPY

(71) Applicant: Physio-Control, Inc., Redmond, WA (US)

(72) Inventor: Joseph L. Sullivan, Kirkland, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

(21) Appl. No.: 15/389,293

(22) Filed: Dec. 22, 2016

(65) Prior Publication Data

US 2017/0136249 A1 May 18, 2017

Related U.S. Application Data

(62) Division of application No. 12/572,691, filed on Oct. 2, 2009, now Pat. No. 9,539,434.

(51) Int. Cl.
*A61N 1/00* (2006.01)
*A61N 1/39* (2006.01)

(52) U.S. Cl.
CPC .......... *A61N 1/3925* (2013.01); *A61N 1/3943* (2013.01); *A61N 1/3987* (2013.01)

(58) Field of Classification Search
CPC ............................ A61N 1/3925; A61N 1/3943
USPC ........................................................ 607/5, 7
See application file for complete search history.

(56) References Cited

U.S. PATENT DOCUMENTS

| | | | |
|---|---|---|---|
| 5,662,690 A | 9/1997 | Cole et al. | |
| 6,269,267 B1 * | 7/2001 | Bardy | A61N 1/39 607/5 |
| 6,334,070 B1 | 12/2001 | Nova et al. | |
| 6,356,785 B1 | 3/2002 | Snyder et al. | |
| 6,553,257 B2 | 4/2003 | Snyder et al. | |
| 7,567,837 B2 | 7/2009 | Weil et al. | |
| 7,580,741 B2 | 8/2009 | Cazares et al. | |
| 7,623,915 B2 | 11/2009 | Sullivan et al. | |
| 7,630,762 B2 | 12/2009 | Sullivan et al. | |
| 2004/0267325 A1 * | 12/2004 | Geheb | A61B 5/11 607/5 |
| 2006/0173500 A1 | 8/2006 | Walker et al. | |
| 2006/0173501 A1 | 8/2006 | Stickney et al. | |
| 2007/0213775 A1 * | 9/2007 | Snyder | A61N 1/3987 607/7 |
| 2008/0027338 A1 | 1/2008 | Lu et al. | |

OTHER PUBLICATIONS

International Search Report and Written Opinion issued in International Application No. PCT/US2009/059371, dated May 7, 2010 (17 pages).

* cited by examiner

*Primary Examiner* — Nadia A Mahmood
(74) *Attorney, Agent, or Firm* — Lane Powell PC

(57) ABSTRACT

Systems, devices, software and methods are provided, for making a decision as to whether to administer an electric shock to a patient. The decision can be made differently, depending on whether the patient has already been shocked or not.

12 Claims, 9 Drawing Sheets

*DEFIBRILLATION SCENE*

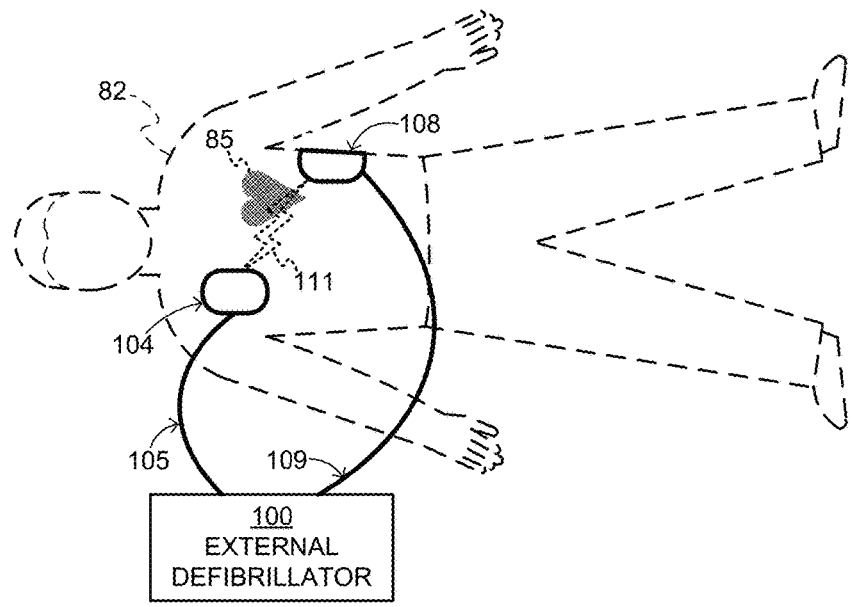
FIG. 1  *DEFIBRILLATION SCENE*
| TYPE OF EXTERNAL DEFIBRILLATOR | INTENDED TO BE USED BY PERSONS: ||
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2  *TWO MAIN TYPES OF EXTERNAL DEFIBRILLATORS*

ITERATIONS DURING SESSION

FIG. 5    *METHODS*

FIG. 7  *METHODS*

SAMPLE REMOVAL OF ARTIFACTS

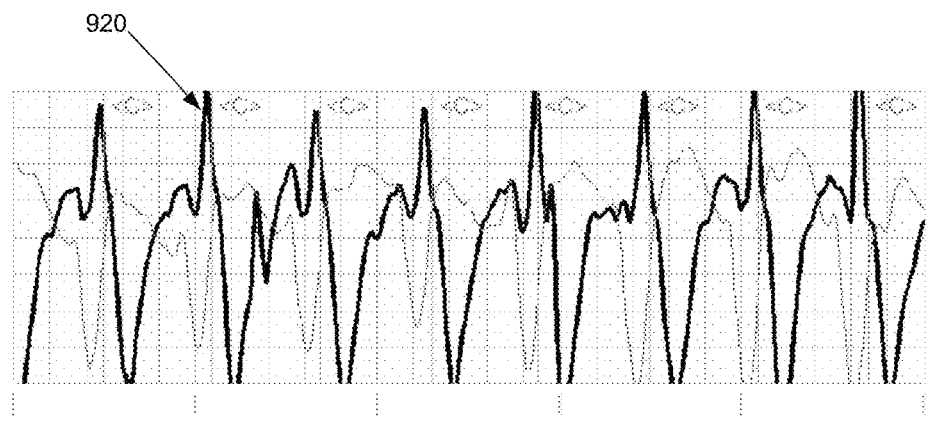
*SAMPLE PATIENT DATA BEFORE AND AFTER ARTIFACT REMOVAL*
FIG. 9

SAMPLE DIFFERENT DECISION MANNERS

DECIDING ON PATIENT ELECTRIC SHOCK THERAPY

CROSS-REFERENCE TO RELATED APPLICATIONS

This application is a division of and claims priority to U.S. Non-Provisional patent application Ser. No. 12/572,691, filed Oct. 2, 2009, entitled DECIDING ON PATIENT ELECTRIC SHOCK THERAPY, the disclosure of which is incorporated herein by reference in its entirety.

FIELD

This invention generally relates to deciding on patient electric shock therapy.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the right sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia, and some of it may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

It is desired to improve patient outcomes, by making improved decisions of when to administer therapy, such as electrical shocks, CPR, pharmaceuticals, etc. Patient outcomes are sometimes analyzed in post-event review.

BRIEF SUMMARY

The present description gives instances of systems, devices, software and methods, the use of which may help overcome problems and limitations of the prior art.

In some embodiments, a decision as to whether to administer an electric shock to a patient is made differently, depending on whether the patient has already been shocked or not. Embodiments include medical devices such as defibrillators and pacers, and also processors, computers, software, and methods of making the decision. The decision can be made in the field, or in a post-event review scenario.

An advantage over the prior art is that patient outcomes can be improved.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 9 is a time diagram of patient data in the form of signals, before and after an artifact removal operation of the flowchart of FIG. 7.

DETAILED DESCRIPTION

Figure 3:
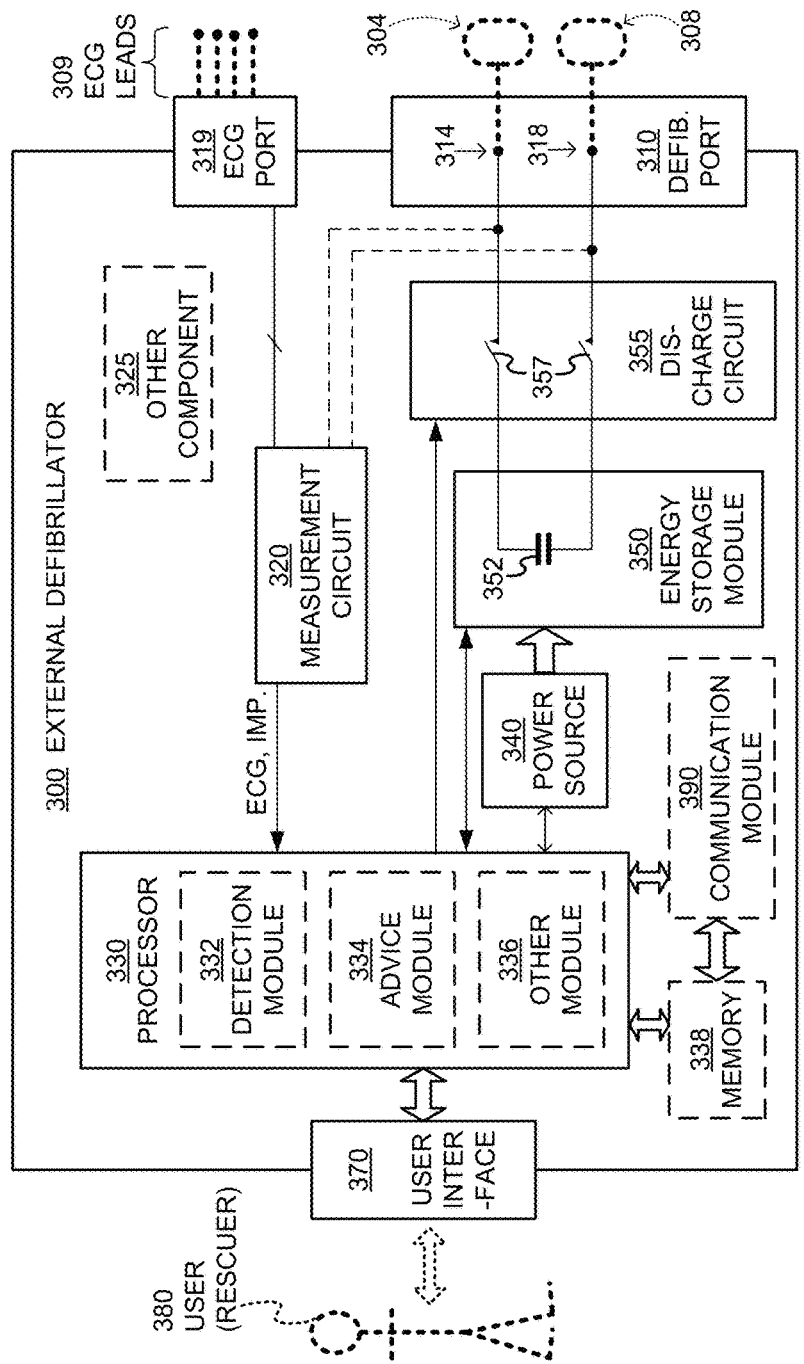
FIG. 3 is a diagram showing components of an external defibrillator, such as the one shown in FIG. 1, which is made according to embodiments.

As has been mentioned, the present description is about making a decision of whether electric therapy should be administered or not. Embodiments include medical devices that can administer electrical therapy, such as defibrillators, pacers, etc. Examples are now described.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a unit with a patient monitor. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological signals of a person in an emergency scenario. For example, these signals can include a person's full ECG (electrocardiogram) signals. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1.

External defibrillator 300 is intended for use by a user 380, who would be the rescuer. Defibrillator 300 typically includes a defibrillation port 310, such as a socket. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319, for plugging in ECG leads 309. ECG leads 309 can sense a full ECG signal. Moreover, a defibrillator-monitor could have additional ports (not shown), and another component 325 for the above described additional features.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

An additional feature of a defibrillator can be CPR-prompting. Prompts are issued to the user, visual or by sound, so that the user can administer CPR. Examples are taught in U.S. Pat. No. 6,334,070 and U.S. Pat. No. 6,356,785.

Figure 4:
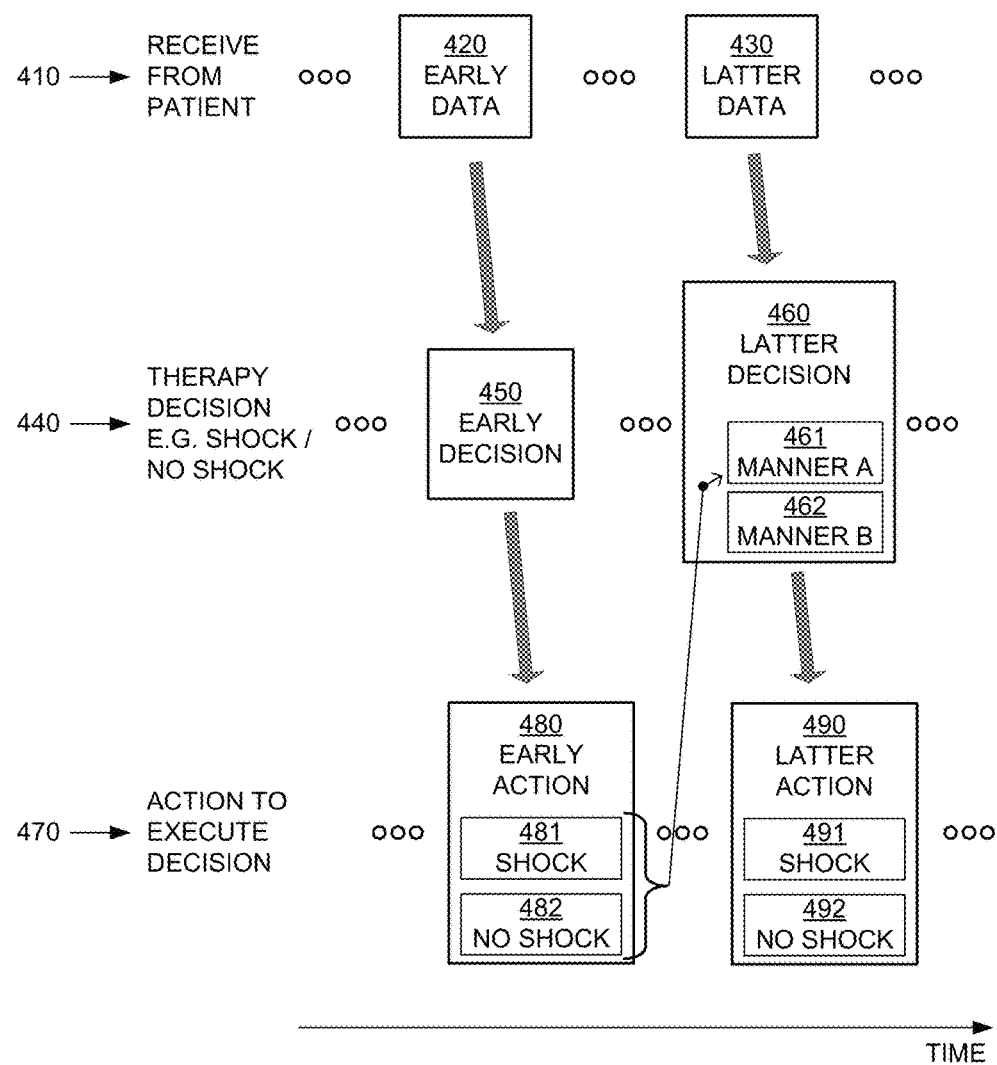
FIG. 4 is a time diagram depicting operations according to embodiments.

FIG. 4 is a diagram depicting operations according to embodiments against a time axis. The operations of FIG. 4 can be considered to be within a single session for a patient. The session can be a session of resuscitation or of mere analysis in post-event review. A session can be defined in any suitable way. One suitable way is when electrodes 104, 108 are first attached to person 82. Other suitable ways will be understood upon reading this document, for example upon inputting prior shock records.

In FIG. 4, a series 410 depicts the relative timing of receiving data that has been collected by the patient. In particular, early data 420 is received before latter data 430. Early data 420 and latter data 430 can include ECG data of the patient, impedance data, other data received while the patient is being monitored, and so on.

A series 440 depicts the relative timing of therapy decisions. In particular, an early decision 450 is made from early data 420, and a latter decision 460 is made from latter data 430. The therapy decisions can be to shock or not, or to perform other therapy, such as to administer CPR, administer pharmaceuticals, etc.

A series 470 depicts the relative timing of actions that execute the decisions of series 440. In particular, an early action 480 carries out early decision 450, and a latter action 490 carries out latter decision 460. Action 480 can be to shock 481, or to not shock 482, for executing decision 450. Similarly, action 490 can be to shock 491, or to not shock 492, for executing decision 460. An embodiment can either administer a shock, or cause a shock to be administered, and so on. Additionally, although represented expressly for completeness, actions 482, 492, may be ways of representing that there is no early or latter action 480, 490, respectively. If the decision is for a different therapy, the action to execute it can be by prompting, etc.

The operations of FIG. 4 can be repeated, as a patient is being monitored via their data, and treated accordingly. In other words, data is collected from the patient, received by the medical device or processor 330, a decision is made to shock or to not shock, the decision is executed, and then the process repeats. The data, decisions, and actions shown in FIG. 4 are only two iterations in a session of such operations. The shown two iterations could be successive, but do not need to be, and other iterations could intervene. Accordingly, the words "early", "latter", and even "latest" in this document are intended as chronologically characterizing the timing of iterations relative to each other. More specifically, the iteration of receiving early data 420, making early decision 450, and taking early action 480 occur prior to collecting data that is received as latter data 430. Plus, a session can be interrupted, etc.

Importantly, latter decision 460 need not be made always the same way. In some embodiments, latter decision 460 is made either according to a first decision manner A 461, or according to a second decision manner B 462. First decision manner A 461 is different from second decision manner B 462. The first decision manner A 461 can be used if no electric shock has been administered to this patient in a previous action, such as early action 480. But if such an electric shock has been administered, then second decision manner B 462 can be used to make latter decision 460.

The electric shock of action 481 need not contain enough energy to defibrillate the patient's heart. It can contain less energy, for example merely enough to pace the heart, or stimulate the myocardium.

What is written above for latter decision 460 could also apply for early decision 450. For example, early decision 450 can be made according to first decision manner A 461, or second decision manner B 462, depending on whether a shock has been administered previously. Or, it can be made consistently according to manner A or manner B. Or it can be made according to an early decision manner that is yet different from the other two.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps which may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods are now described.

Figure 5:
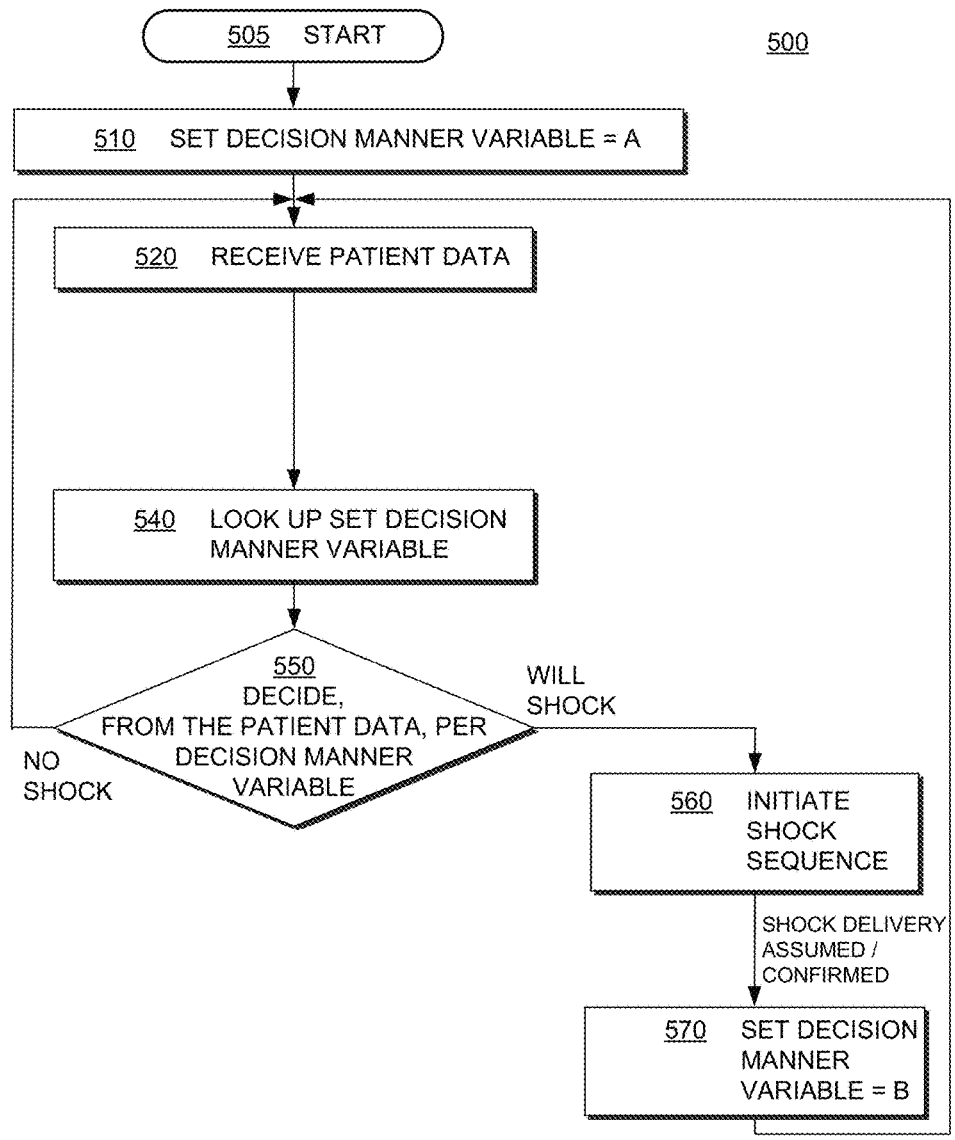
FIG. 5 is a flowchart for illustrating methods according to embodiments.

FIG. 5 shows a flowchart 500 for describing methods according to embodiments. The methods of flowchart 500 may also be practiced by systems, devices, and software according to embodiments.

From a start space 505, according to an operation 510, a decision manner variable is set at a value A. While other examples are also possible, it will be recognized that this value A could be for implementing first decision manner 461A of FIG. 4.

According to a next operation 520, patient data is received. This can be performed in a number of ways. In a sample embodiment, the patient data is early data 420 of FIG. 4.

According to a next operation 540, the set decision manner variable is looked up, from how it was set last. In this description of FIG. 5, the set decision manner variable was last set in operation 510, at value A.

According to a next operation 550, a decision is made as to whether an electric shock should be administered to the patient or not. As will be evident from this document, the decision could further be in other outcomes, such as other therapies, etc. The decision of operation 550 can be made from the patient data received at operation 520, and also according to the value of the decision manner variable that was looked up at operation 540. In other words, a different decision can be reached from a single set of patient data depending on the decision manner variable, as will be described in more detail later in this document.

If at operation 550 the decision is that no shock should be administered, execution returns to operation 520. Additional data is thus received, and then at operation 540 the decision manner variable is looked up again, except its value can be the same, since it has not been updated. Then operation 550 is reached again, etc. The sequence of operations described so far can be independent of whether the patient is receiving other treatment, like CPR and the like. The decision to not shock, in this example, might not interfere with the other treatment.

If at operation 550 the decision is that a shock should be administered, according to a next operation 560, such a shock is indeed caused to be administered. At that point, the delivery of the electric shock can be assumed, or even confirmed by the appropriate input.

According to a next operation 570, decision manner variable is set at a value B, different from A. While other examples are also possible, it will be recognized that this value B could be for implementing second decision manner 462B of FIG. 4.

Execution then returns to operation 520. Additional data is thus received, but when at operation 540 the last value of the decision manner variable is looked up again, its value can be different, since it has been updated. Then operation 550 is reached again, and so on.

These iterations can be repeated, as was described already with reference to FIG. 4. For example, even after shocking and updating the decision manner variable, the next iteration could make the decision to shock again. At that time, the decision manner variable can remain at value B, or be further updated to a third value corresponding to a third decision manner, and so on.

Operation 550 can be performed in a number of ways. For example, in operation 460, first decision manner A 461 can be to use one shock advisory algorithm, while second decision manner B 462 can be to use a different shock advisory algorithm.

In other embodiments, a single algorithm is used for both decision manners, but differently for each of the different decision manners. For example, a scoring parameter can be computed from the patient data by the algorithm. For each decision manner, the scoring parameter would have to meet different conditions, for deciding whether the shock should be administered or not. For example, first decision manner A 461 can include to decide that the shock should be administered if the scoring parameter meets a first condition, but should not be administered otherwise. And second decision manner B 462 can include to decide that the shock should be administered if the scoring parameter meets a second condition, but should not be administered otherwise.

A number of types of conditions can be used, which would be different for the two different decision manners. An example is now described.

Figure 6:
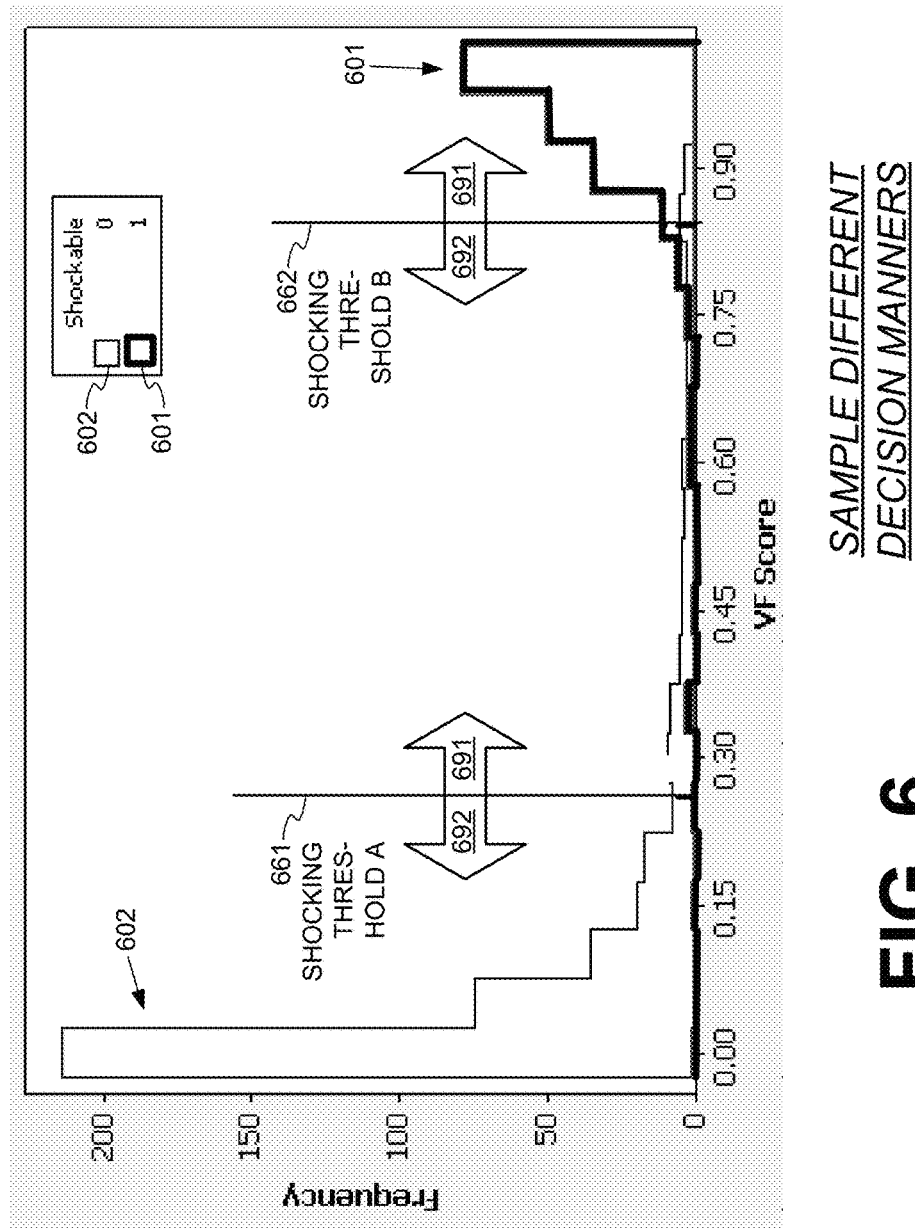
FIG. 6 is a diagram showing an embodiment of how a scoring parameter is mapped against known patient data, and of how different decision manners of the methods of FIG. 5 can be embodied by different shocking thresholds for the scoring parameter.

FIG. 6 is a diagram showing an embodiment of where the scoring parameter is called a "VF Score". The VF Score is computed according to an algorithm from the received patient data. FIG. 6 further plots, in terms of the VF Score, the frequencies of known non-shockable data 602, and known shockable data 601. The two different conditions can be implemented by two different shocking thresholds 661, 662. The action can be to shock 691 or to not shock 692, depending on which shocking threshold is being used.

A frequent challenge is that sometimes the patient data is ECG data, which is collected while the patient is receiving chest compressions. In those instances, the ECG data may have been corrupted by one or more artifacts that is caused by the chest compressions. Embodiments are now described for dealing with the challenge.

Figure 7:
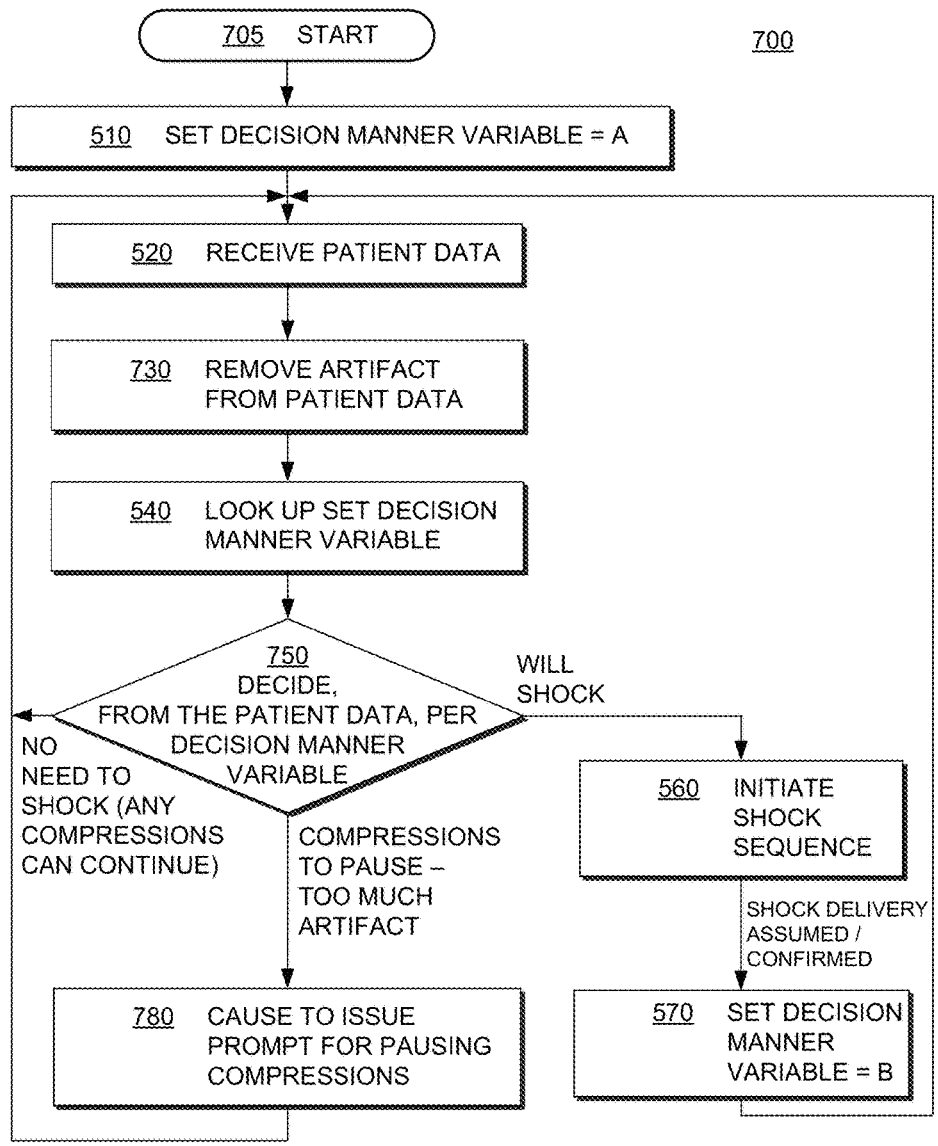
FIG. 7 is a flowchart for illustrating additional methods according to embodiments.

FIG. 7 shows a flowchart 700 for describing additional methods according to embodiments. It will be recognized that flowchart 700 uses many of the operations of previously described flowchart 500. Indeed, from a start space 705, operations 510 and 520 are performed, with the patient data being ECG data.

According to a next operation 730, at least one artifact is removed from the patient data of operation 520. The artifact can be removed in any number of ways, mostly characterized by how it becomes known. In some embodiments, the artifact is collected independently from the ECG data, for example by using force sensors, pressure sensors, accelerometers, and the like to measure aspects of the chest compressions. In other embodiments, the artifact is derived from the ECG data itself. An example is now described.

Figure 8:
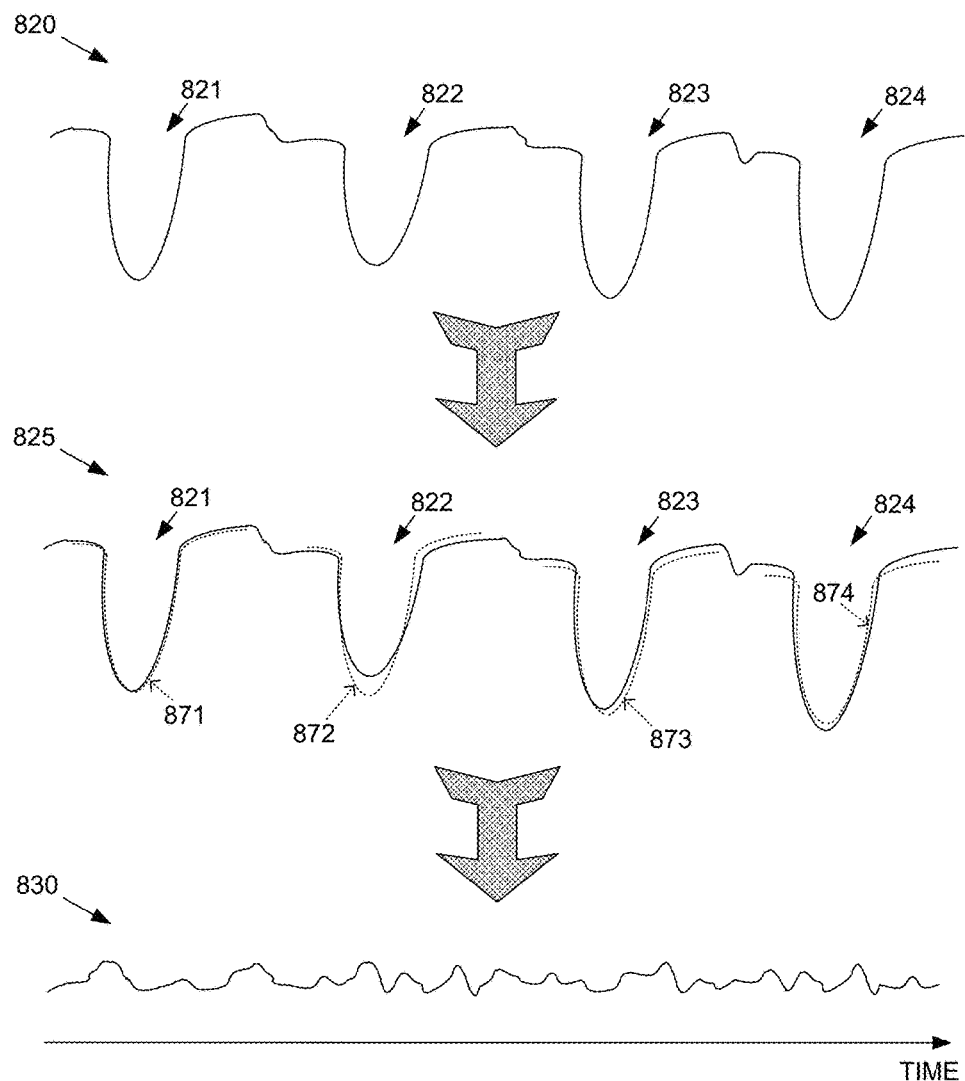
FIG. 8 is a time diagram of a sample embodiment of an artifact removal operation of the flowchart of FIG. 7.

FIG. 8 is a time diagram where patient data 820 is shown as a signal. A number of artifacts 821, 822, 823, 824 in patient data 820 are caused by chest compressions. A statistical artifact is computed from artifacts 821, 822, 823, 824. As shown in iconic signal 825, the statistical artifact is then modified to fit to individual artifacts 821, 822, 823, 824, in the form of respective corrections 871, 872, 873, 874. Further, signal 830 reflects the patient data, after corrections 871, 872, 873, 874 have indeed been removed. Signal 830 is sometimes called a remainder signal.

Returning to FIG. 7, after operation 730, the previously described operation 540 is performed. According to a next operation 750, a decision is made as to whether an electric shock should be administered to the patient or not. The decision of operation 750 can thus be made from the patient data received at operation 520, as improved by operation 730, and also according to the value of the decision manner variable that was looked up at operation 540. In addition, if the shock/no shock decision cannot be reached with a high enough confidence, a request can be made that the compressions be paused. Examples are now described.

If at operation 750 the decision is that a shock should be administered, execution proceeds to operations 560, 570, and then back to 520, similarly to what was described above for flowchart 500.

If at operation 750 the decision is that no shock should be administered, execution returns to operation 520, as in flowchart 500. An example is seen in FIG. 9 where, from patient data 920, a remainder signal 930 has been derived after removal of artifact. By analyzing remainder signal 930, it is determined that no shock need be administered. It will be understood that the sample signals of FIG. 9 are actually occurring signals, while those of FIG. 8 are only iconic to illustrate mechanics of artifact removal.

The decision that no shock should be administered would not always be as clear-cut as may be suggested by sample remainder signal 930. In some instances the artifact can be so large that removal techniques, however sophisticated, do not succeed in rendering a remainder signal that is good enough for the shock/no shock determination to be made with a high enough confidence.

Returning to FIG. 7, at operation 750 the corresponding decision can be that a shock should be not be administered, but compressions should pause. So, when a confidence condition is not met, execution can be routed through operation 780 first, and then back to operation 520. According to operation 780, a prompt is caused to be issued for the rescuer to pause the chest compressions. The prompt can be visual or auditory, e.g. via interface 370. The rescuer will pause the compressions, the artifact will no longer be generated, and the next iteration of receiving collected patient data, analyzing, and deciding will permit a shock/no shock determination with improved confidence.

According to optional embodiments, the confidence condition can be further different for first decision manner A 461 than for second decision manner B 462. This can be implemented in any number of ways. For example, a confidence score can be computed, the confidence condition can be that the confidence score is less than a confidence threshold, and that the confidence threshold is different for first decision manner A 461 than for second decision manner B 462.

In some embodiments, the previously mentioned scoring parameter that is used with the shocking thresholds is also used as the confidence score. An example is now described.

Figure 10:
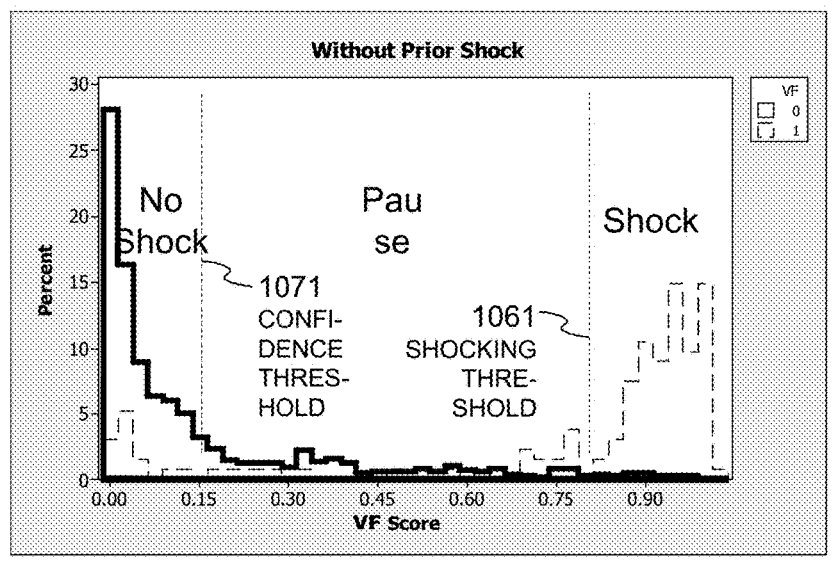
FIGS. 10 and 11 are diagrams for showing how a scoring parameter can be used for making shock/no shock determinations and further serve in determining whether a non-shock determination is made with adequate confidence, and contrasting how these determinations can be different in different decision manners.
Figure 11:
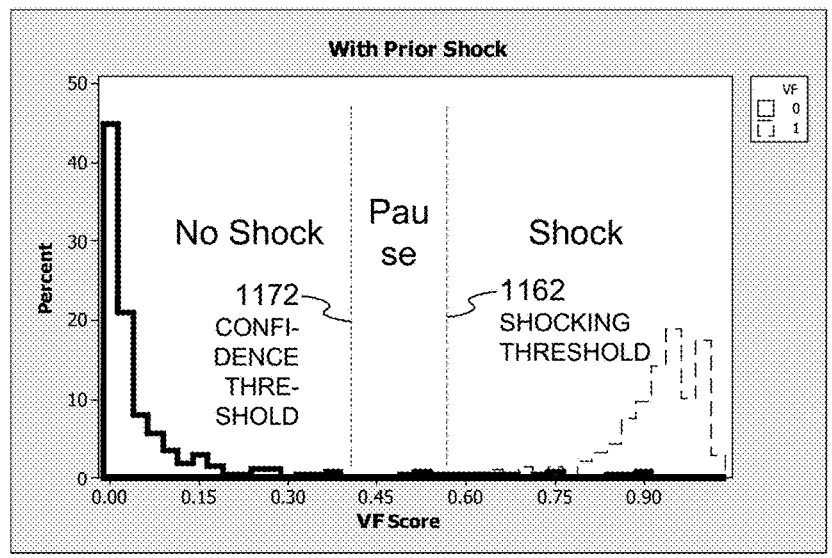

FIGS. 10 and 11 are diagrams similar to FIG. 6, for showing how a scoring parameter can be used for making shock/no shock determinations, and further serve in determining whether a non-shock determination is made with adequate confidence. In these examples the scoring parameter is the VF score, which also serves as a reverse confidence score. "Reverse", in the sense that the higher the VF score, the less the confidence in the outcome, and thus the higher the chance that a pause in the compressions will be needed.

FIGS. 10 and 11 also contrast different decision manners. FIG. 10 can correspond to decision manner A 461 before a shock has been administered, while FIG. 11 can correspond to decision manner B 462 after a shock has been administered.

In particular, FIG. 10 is a diagram showing how the VF score can fall in one of three ranges, which drives the decision of operation 750. If the VF score is higher than a shocking threshold 1061, then a shock should be administered. If it is lower than a confidence threshold 1071, then there is no shock, but there is no prompting of the compressions to stop. And if it is in between thresholds 1071 and 1061, there is no shock, but a pause in the compressions is requested so that a better analysis and decision can be made in the next iteration.

Similarly, FIG. 11 shows how the same VF score can fall in one of three ranges. Thresholds 1172, 1162 correspond to thresholds 1071 and 1061, but have been moved, effectuating a different decision manner.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:

1. A method, comprising:
   receiving latter data collected from a patient during a session, wherein the latter data comprises ECG data collected while the patient has been receiving chest compressions; and
   deciding from the latter data whether a latter electric shock should be administered or not to the patient, the decision being according to a first decision manner if no early electric shock has been administered to the patient during the session prior to when the latter data was collected, and according to a second decision manner different from the first decision manner otherwise, in which;
a scoring parameter is computed from the latter data by an algorithm,
deciding according to the first decisions manner includes deciding that the latter shock should be administered if the scoring parameter meets a first condition, but should not be administered otherwise, the first condition being that the scoring parameter is larger than a first shocking threshold;
deciding according to the second decision manner includes deciding that the latter shock should be administered if the scoring parameter meets a second condition being different from the first condition, the second condition being that the scoring parameter is larger than a second shocking threshold different from the first shocking threshold, and further in which;
a confidence score is computed,
a confidence condition is not met if the confidence score is less than a confidence threshold,
the confidence threshold is different for the first decision manner than the second decision manner, and
when it is decided that the latter shock should not be administered, a prompt is caused to be issued for pausing the chest compressions if the confidence condition is not met.

2. The method of claim 1, further comprising:
receiving early data collected from the patient during the session but before the latter data was collected; and
deciding from the early data whether the early electric shock should be administered or not to the patient.

3. The method of claim 2, further comprising:
if it is decided that the early electric shock should be administered, causing the early electric shock to be administered.

4. The method of claim 2, in which
it is decided whether the early electric shock should be administered or not according to the first decision manner.

5. The method of claim 2, in which
it is decided whether the early electric shock should be administered or not according to an early decision manner that is different from the first decision manner.

6. The method of claim 1, further comprising:
if it is decided that the latter electric shock should be administered, causing the latter electric shock to be administered.

7. The method of claim 6, further comprising:
receiving latest data collected from the patient after the latter electric shock has been administered; and
deciding from the latest data whether a latest electric shock should be administered or not to the patient, the decision being according to a third decision manner different from the second decision manner.

8. The method of claim 1, in which
the decision according to the first decision manner includes using a different algorithm than the second decision manner.

9. The method of claim 1, in which
an artifact caused by the chest compressions is further removed from the latter data.

10. The method of claim 9, in which
the artifact is collected independently from the ECG data.

11. The method of claim 9, in which
the artifact is derived from the ECG data.

12. An article comprising: a storage medium, the storage medium having instructions stored thereon, in which when the instructions are executed by a processor, they result in:
receiving latter data collected from a patient during a session, wherein the latter data comprises ECG data collected while the patient has been receiving chest compressions; and
deciding from the remaining signal whether a latter electric shock should be administered or not to the patient, the decision being according to a first decision manner if no early electric shock has been administered to the patient during the session prior to when the latter data was collected, and according to a second decision manner different from the first decision manner otherwise, in which;
a scoring parameter is computed from the latter data by an algorithm,
deciding according to the first decisions manner includes deciding that the latter shock should be administered if the scoring parameter meets a first condition, but should not be administered otherwise, the first condition being that the scoring parameter is larger than a first shocking threshold;
deciding according to the second decision manner includes deciding that the latter shock should be administered if the scoring parameter meets a second condition being different from the first condition, the second condition being that the scoring parameter is larger than a second shocking threshold different from the first shocking threshold, and further in which;
a confidence score is computed,
a confidence condition is not met if the confidence score is less than a confidence threshold,
the confidence threshold is different for the first decision manner than the second decision manner, and
when it is decided that the latter shock should not be administered, a prompt is caused to be issued for pausing the chest compressions if the confidence condition is not met.

* * * * *